(12) United States Patent
Zhang et al.

(10) Patent No.: US 12,257,084 B2
(45) Date of Patent: Mar. 25, 2025

(54) MOTION FREE CT SAMPLING WITH ELECTRON BEAM SCANNING AND TIME DELAY INTEGRATION DETECTOR

(71) Applicant: Washington University, St. Louis, MO (US)

(72) Inventors: Tiezhi Zhang, St. Louis, MO (US); Qinghao Chen, St. Louis, MO (US); Shuang Zhou, St. Louis, MO (US); Yuewen Tan, St. Louis, MO (US)

(73) Assignee: Washington University, St. Louis, MO (US)

( * ) Notice: Subject to any disclaimer, the term of this patent is extended or adjusted under 35 U.S.C. 154(b) by 241 days.

(21) Appl. No.: 18/053,551

(22) Filed: Nov. 8, 2022

(65) Prior Publication Data

US 2023/0141925 A1      May 11, 2023

Related U.S. Application Data (60) Provisional application No. 63/276,827, filed on Nov. 8, 2021.

(51) Int. Cl.
| | |
|---|---|
| *A61B 6/02* | (2006.01) |
| *A61B 6/00* | (2006.01) |
| *A61B 6/03* | (2006.01) |
| *A61B 6/40* | (2024.01) |
| *A61B 6/42* | (2024.01) |

(52) U.S. Cl.
CPC .............. *A61B 6/032* (2013.01); *A61B 6/027* (2013.01); *A61B 6/4021* (2013.01); *A61B 6/4028* (2013.01); *A61B 6/4085* (2013.01); *A61B 6/4233* (2013.01); *A61B 6/4435* (2013.01)

(58) Field of Classification Search
None
See application file for complete search history.

(56) References Cited

U.S. PATENT DOCUMENTS

| | | | | |
|---|---|---|---|---|
| 5,625,661 A * | 4/1997 | Oikawa | ............... | A61B 6/4085 378/19 |
| 5,841,829 A * | 11/1998 | Dolazza | ............... | A61B 6/4021 378/11 |
| 6,256,369 B1 * | 7/2001 | Lai | ............... | A61B 6/4028 378/9 |
| 7,421,059 B2 | 9/2008 | Suzuki et al. | | |
| 7,764,763 B2 * | 7/2010 | Mori | ............... | A61B 6/027 378/19 |
| 8,571,172 B2 * | 10/2013 | Dafni | ............... | A61B 6/032 378/11 |
| 8,774,354 B2 * | 7/2014 | Ullberg | ............... | H04N 25/711 378/197 |
| 8,848,999 B2 * | 9/2014 | Boese | ............... | A61B 6/4007 382/131 |

(Continued)

*Primary Examiner* — Thomas R Artman
(74) *Attorney, Agent, or Firm* — Armstrong Teasdale LLP (57) ABSTRACT

A CT scanning method compensates gantry motion blurring in projection measurement based on synchronized focal spot movement and detector data shifting. Tube power is increased by moving the focal on the target and reducing focal spot dwell duration. The CT scanning method is used on helical CT and cone beam with a rotating anode source and CBCT and TBCT with a linear array x-ray source.

5 Claims, 9 Drawing Sheets
(1 of 9 Drawing Sheet(s) Filed in Color)

(56) References Cited

U.S. PATENT DOCUMENTS

| | | | |
|---|---|---|---|
| 8,983,024 B2* | 3/2015 | Zhang | A61B 6/466 |
| | | | 378/22 |
| 9,153,411 B2* | 10/2015 | Boese | A61B 6/4435 |
| 9,659,739 B2* | 5/2017 | Bathe | H01J 35/147 |
| 10,455,678 B2* | 10/2019 | Zhang | H04N 23/30 |
| 10,799,193 B2 | 10/2020 | Ghazi et al. | |
| 2005/0117696 A1* | 6/2005 | Suzuki | A61B 6/548 |
| | | | 378/19 |
| 2009/0168952 A1* | 7/2009 | Mori | A61B 6/027 |
| | | | 378/15 |
| 2011/0033024 A1* | 2/2011 | Dafni | A61B 6/027 |
| | | | 378/11 |
| 2011/0268341 A1* | 11/2011 | Boese | G06T 11/006 |
| | | | 977/950 |
| 2012/0014503 A1* | 1/2012 | Ullberg | H04N 25/711 |
| | | | 378/19 |
| 2012/0163531 A1* | 6/2012 | Zhang | A61B 6/025 |
| | | | 378/9 |
| 2013/0034201 A1 | 2/2013 | Boese et al. | |
| 2015/0098548 A1* | 4/2015 | Bathe | H01J 35/30 |
| | | | 378/62 |
| 2018/0343728 A1 | 11/2018 | Zhang et al. | |
| 2019/0179040 A1 | 6/2019 | Luu et al. | |
| 2020/0253567 A1* | 8/2020 | Ghazi | A61B 6/032 |
| 2023/0141925 A1* | 5/2023 | Zhang | A61B 6/4435 |
| | | | 378/4 |

* cited by examiner

MOTION FREE CT SAMPLING WITH ELECTRON BEAM SCANNING AND TIME DELAY INTEGRATION DETECTOR

STATEMENT REGARDING FEDERALLY SPONSORED RESEARCH & DEVELOPMENT

This invention was made with government support under EB026401 awarded by the National Institutes of Health. The government has certain rights in the invention.

FIELD OF THE DISCLOSURE

The field of the disclosure relates generally to computed tomography (CT) scanning and, more specifically, a CT scanning method that compensates gantry motion blurring in projection measurement based on synchronized focal spot movement and detector data shifting.

BACKGROUND

An X-ray imaging source produces x-ray photons by bombarding a high z refractory target (e.g., tungsten) with an electron beam. Bremsstrahlung x-ray production is very inefficient with only 1-2% of electron kinetic energy being converted into x-ray and the rest become heat. To achieve sufficient x-ray flux, a computed tomography (CT) tube usually has a power as high as 100 kW. To achieve high resolution, the focal spot of the x-ray sources is small (e.g., less than 1 mm). When bombarding on a target, the kilo-voltage electrons cannot travel deep in the target. Most electrons stop and release their energy within a 5-10 micron depth. Thereby, the focal spot temperature will show a rapid temperature spike and the electron beam's dwell duration needs to be very short to avoid melting the target. For this reason, high power tubes employ a rotating anode to reduce focal spot dwell duration. The dwell duration of rotating anode is the focal spot width divided by the anode linear speed. To have a high linear speed, the anode of x-ray tube has very high rotation speed (e.g., 1000 RPM). Additionally, CT tubes with rotating anode are very complex, expensive and have a short lifetime.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

The present embodiments may relate to, inter alia, systems and methods for diagnostic (helical) computed tomography (CT) as well as cone beam CT (CBCT) and tetrahedron beam CT (TBCT). The present embodiments provide a design aimed to solve two major challenges of current CT, CBCT and TBCT designs: 1) Limited tube output (power) due to focal spot power density and anode rotating speed; and 2) System motion blurring during x-ray sampling through subject. To mitigate the challenge #1, CT system has to slow down rotation speed, which may cause image artifact by organ motion; To mitigate the challenge #2, current CT systems can increase sampling speed or use pulsed x-ray. Increase sampling speed is limited by the detector speed, also increase computation cost in image reconstruction; using pulsed x-ray needs higher power tube as the source has a low duty cycle. The systems and methods of the present embodiments overcome the aforementioned drawbacks by moving the focal spot and shifting the detector data in the same linear speed but opposite direction of gantry rotation, thereby the x-ray beams remain static relative to the imaging object during a projection measurement. For fixed anode tubes, such as the linear array x-ray source of TBCT, the dwell duration of focal spot on the target will be equal to the focal spot width divided by the linear speed of the source due to rotation. For the rotating anode source of helical CT, the focal spot will move against the anode rotation direction, so that the dwell duration equals to the focal spot width divided by the sum of gantry and anode rotating speed.

According to one aspect of this disclosure, a computed tomography (CT) system includes an x-ray source, a 2D detector that performs projection measurement while focal spots move in a same speed and an opposite direction of a gantry rotation, and a time-delay-integration detector configured to shift data in the same speed and the opposite direction of the gantry rotation.

Another aspect of the disclosure is linear array x-ray source for a computed tomography (CT) system. The linear array x-ray source comprises a fixed anode, and focal spots that are moving repeatedly relative to an array direction.

According to still another aspect of the disclosure, a method for performing computed tomography (CT) includes producing x-ray photons with an x-ray source and moving focal spots in a same speed and an opposite direction of a gantry rotation. Projection measurement is performed with a 2D detector while the focal spots move in a same speed and an opposite direction of a gantry rotation, and data is shifted in the same speed and the opposite direction of the gantry rotation using a time-delay-integration detector.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The figures described below depict various aspects of the systems and methods disclosed therein. Each figure depicts an embodiment of a particular aspect of the disclosed systems and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and are instrumentalities shown.

The figures depict preferred embodiments for purposes of illustration only. One skilled in the art will readily recognize from the following discussion that alternative embodiments of the systems and methods illustrated herein may be employed without departing from the principles described herein.

DETAILED DESCRIPTION

The present embodiments are related to, inter alia, diagnostic, or helical, computed tomography (CT). In one exemplary embodiment, a CT scanning method is provided that compensates gantry motion blurring in projection measurement based on synchronized focal spot movement and detector data shifting. Not only removing gantry motion blurring, this technique may also increase the tube power by moving the focal spot on the target and reducing focal spot dwell duration. Additionally, this method may be used on helical CT with a rotating anode source and TBCT with a linear array x-ray source.

Figure 1A:
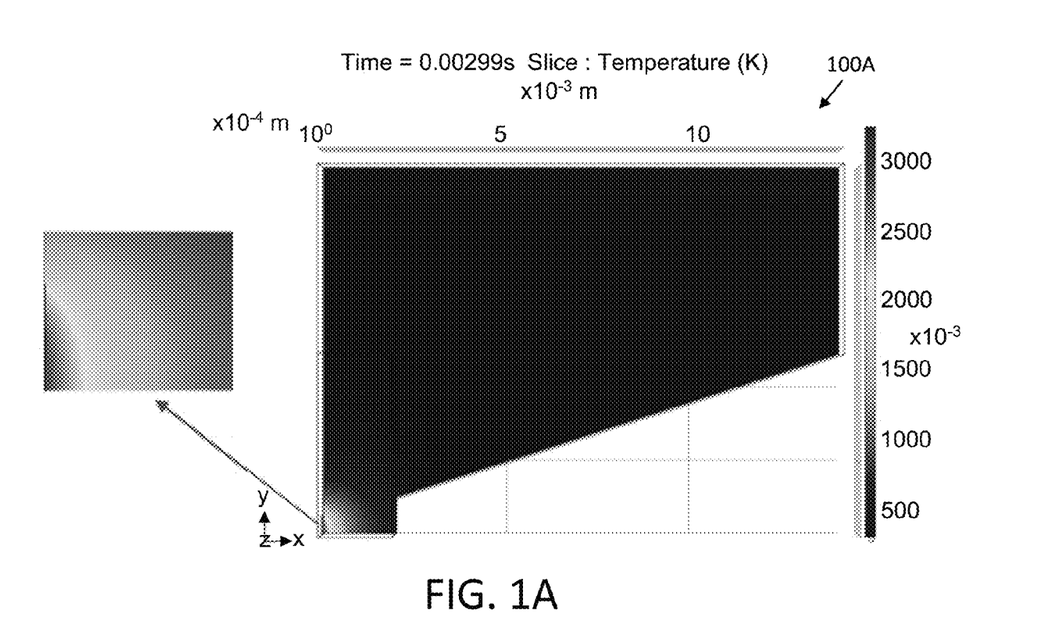
FIG. 1A is an exemplary focal spot temperature distribution.
Figure 1B:
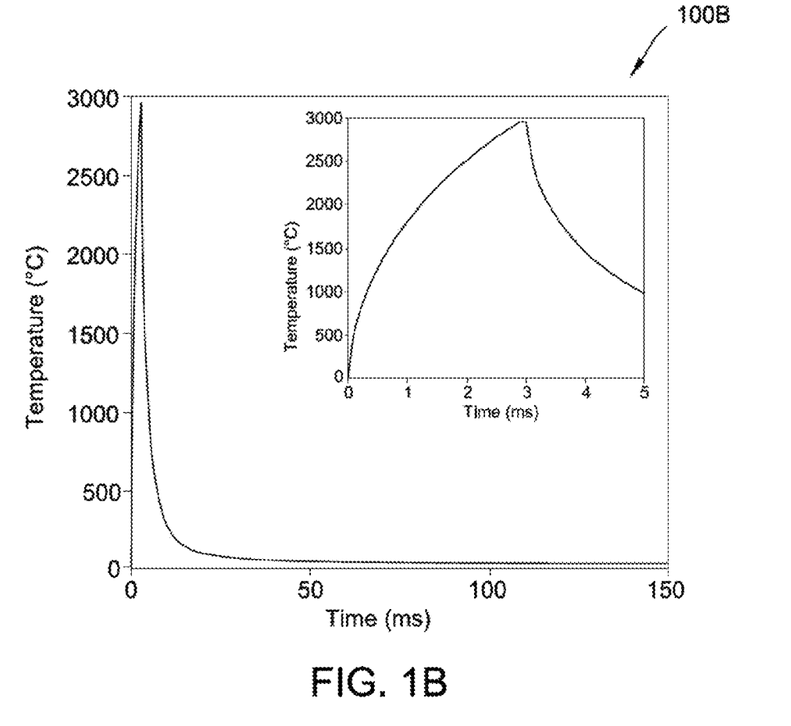
FIG. 1B is an exemplary temperature spike of a focal spot for a 3 ms pulse.
Figure 1C:
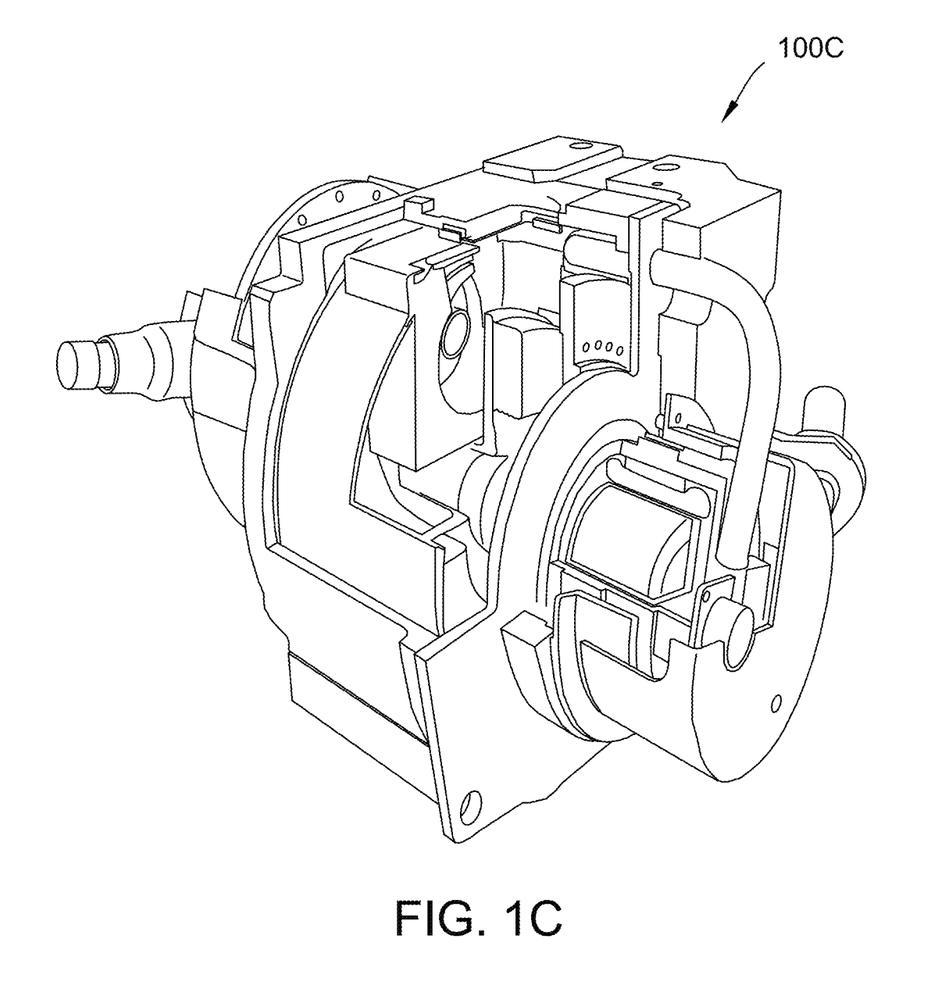
FIG. 1C is an exemplary computed tomography (CT) tube with a rotating anode.

In reference to FIGS. 1A-1C, heat may be deposited, for example, to a very small focal spot and a very shallow depth as shown in diagram 100A. In this example, the focal spot temperature may rise rapidly to its melting point. X-ray sources typically employ a rotation so that the focal spot only stays on the target for a short dwell duration that equals the focal spot width divided by the target linear speed. Continuing with this example, to reduce dwell duration, the anode rotates very fast and also has a large mass in order to have a large heat capacity or heat unit (HU).

Figure 2A:
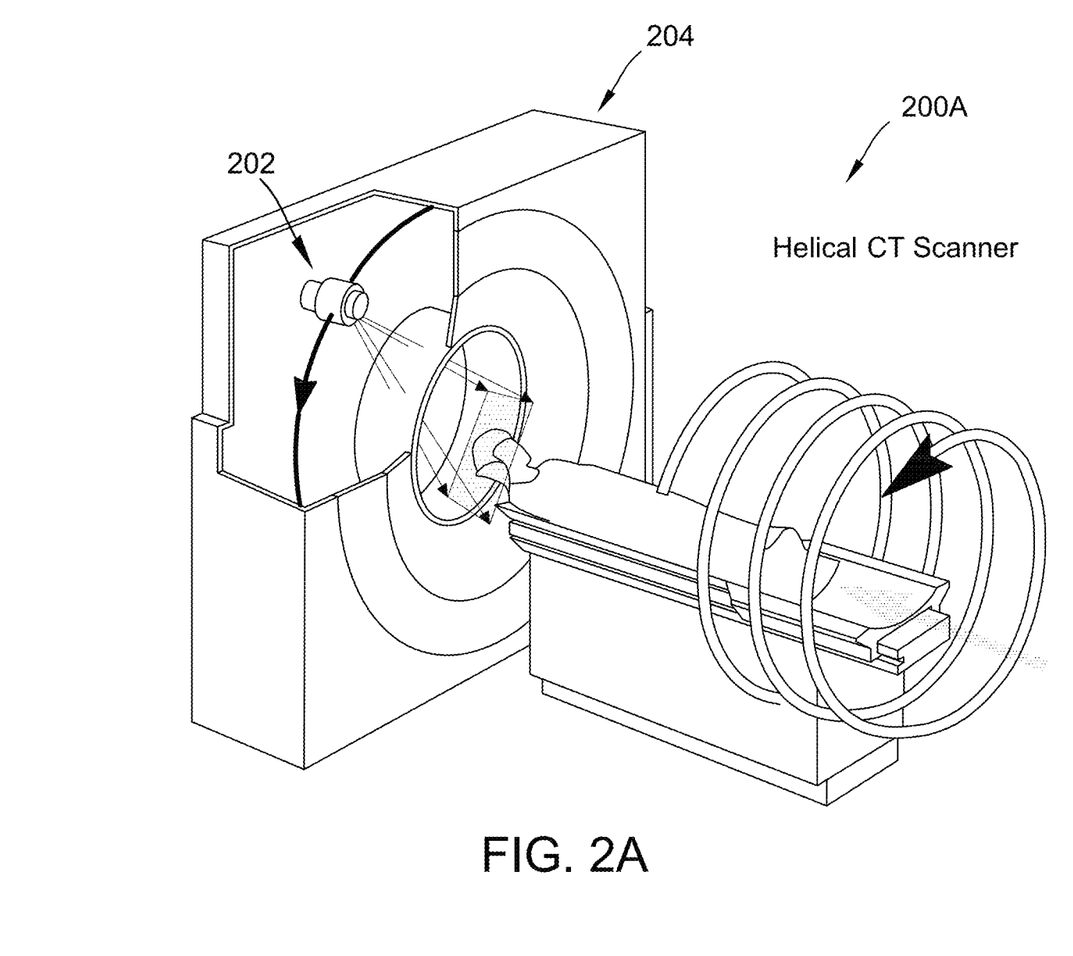
FIG. 2A is an exemplary Helical CT scanner.
Figure 2B:
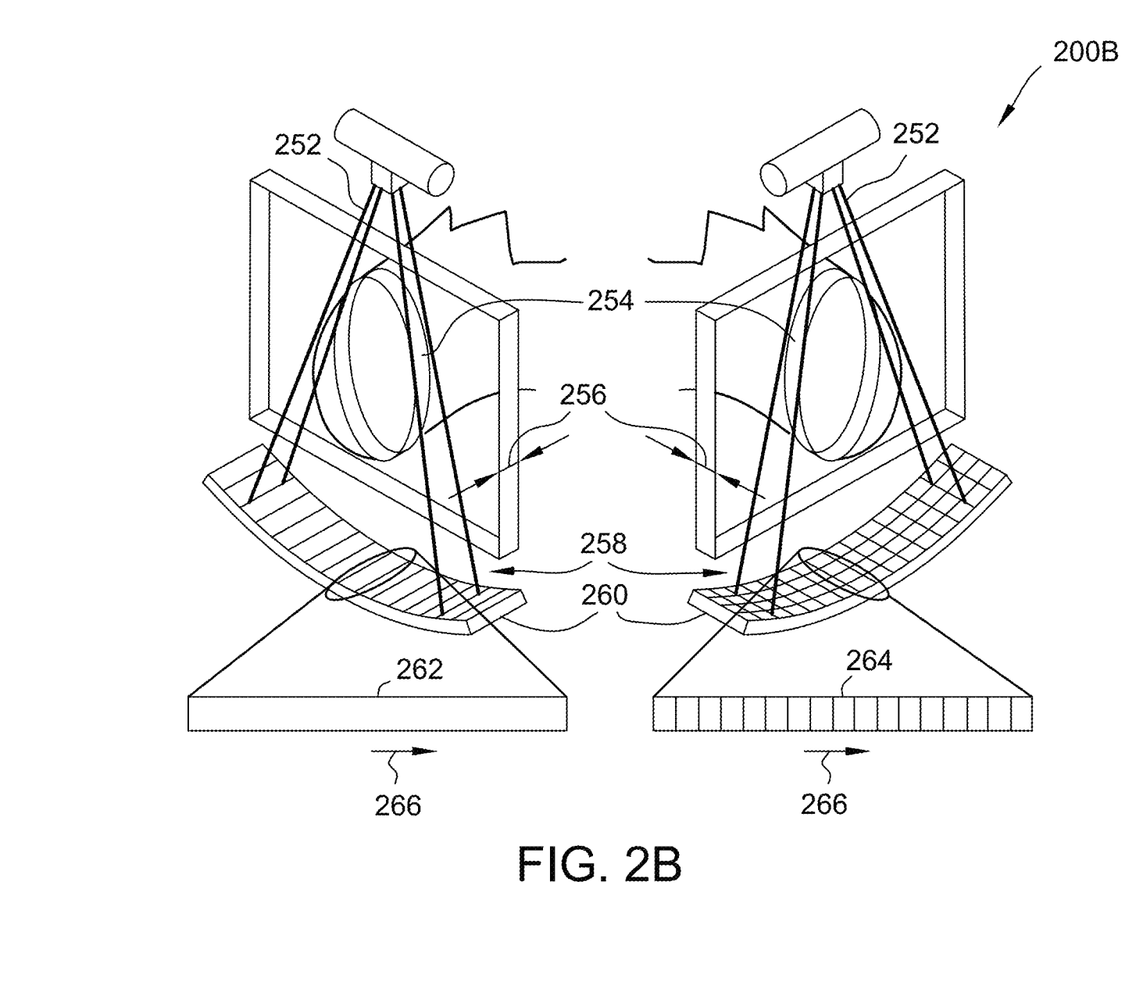
FIG. 2B is components of the Helical CT scanner of FIG. 2A.

FIGS. 2A and 2B show the principle of diagnostic helical CT in accordance with at least one embodiment with respect to a Helical CT Scanner 200A and components diagram 200B. An x-ray source 202 and multi-row detector may be mounted on a fast-rotating gantry 204, the x-ray beam is collimated into a fan shape beam and received by the detector after passing through the patient. In each rotation, the x-ray beam 252 generates hundreds or even over a thousand projection images along a plane. The table translates into the beam and one or more slice of images, or scanned slice 254, may be reconstructed depending on the detector row number. Scanned slice 254 may be of a plane having a slice plane thickness 256. Additionally, the beam may have an x-ray beam thickness 258. In some embodiments, a single slice may include one long detector 262. Additionally, or alternatively, multiple small detectors 264 may be provided. Detectors 262 and 264 of array 260 may be positioned along a z-axis 266. To avoid motion blurring due to cardiac and respiratory movement, the gantry may be rotated very fast, for example, above 3 rev/s. Fast gantry rotation may require the tube 100C (shown in FIG. 1C) to have an extremely high power and to be very sturdy due to the tremendous centrifugal forces. Additionally, or alternatively, because the table movement may be slow, the detector array 260 may need to be wide enough to cover the whole heart so that the whole heart can be covered in one gantry rotation. In some embodiments, a wide detector array 260 may be very expensive as the cost of a CT detector is proportional to the number of detector channels.

To achieve high resolution, the detector and x-ray focal spot may be very small (e.g., <1 mm). The detector 260 may have limited readout speed due to the intrinsic detector response speed (i.e. scintillator speed) or data readout rate, for example. The x-ray beam 252 and detector 260 may move a considerable distance during one projection measurement. For example, if 1000 projections are acquired in one rotation, and the source to central axis distance is 65 cm, the source may move about 4 mm, much larger than focal spot size. Further increase of detector speed may increase number of projection measurement per rotation and reduce source travel distance but may be limited by the intrinsic speed of the detector 260. Mathematically it is unnecessary to use too many projection images for image reconstruction.

In some embodiments, a CT scan may be provided. In a CT scan, each detector may sample x-ray attenuation of the human body along the line between the source and detector. A reconstruction of a cross-section image may require projection measurement from hundreds to over a thousand projection angles. In each sampling, each detector may need to receive a sufficient number of photons to reduce the quantum noises due to stochastic nature of x-ray interaction with tissue. Thereby the x-ray tube may need to have a very high tube power when the gantry rotates fast. In order to reduce motion artifact, the CT gantry may rotate at a fast rate of speed. Thereby the source and detector may move a considerable distance during a projection measurement. Further, the sampling measurement may be blurred by the system rotation motion. Increasing detector framerate and number projection angles may reduce the motion blurring. In an example embodiment, the detector frame rate may be limited by data readout rate and detector response speed (i.e., scintillator speed). Additionally, or alternatively, another approach to freeze motion is to use pulsed x-ray. The x-ray source may need to have a higher power to generate the same number of photons in shorter pulse. Tube power may limited by the focal spot power density and cannot increase indefinitely. Further, too many projection measurements may also increase computation load during reconstruction.

Figure 3A:
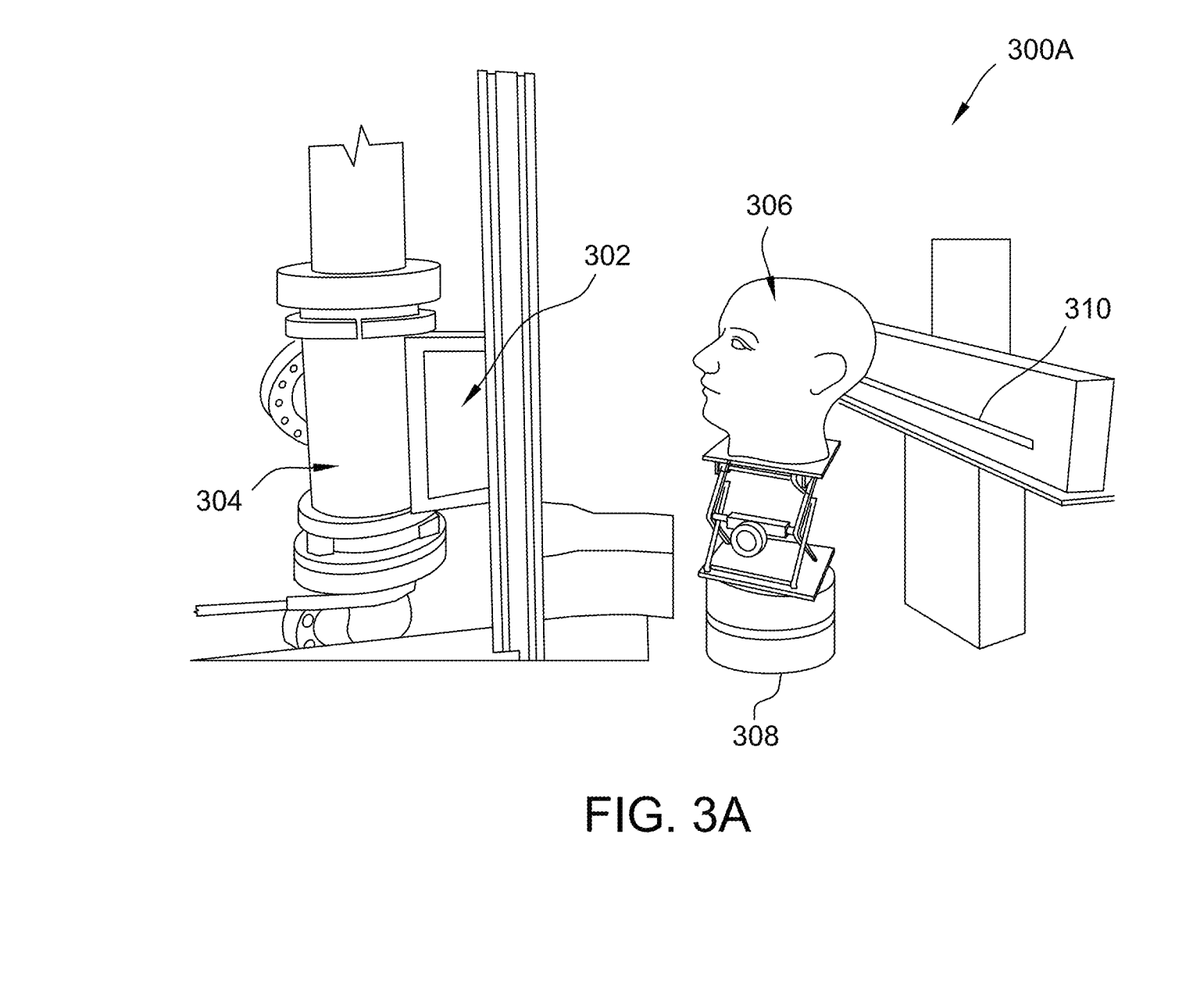
FIGS. 3A-3C is an exemplary Tetrahedtron beam CT (TBCT) scanner benchtop prototype.

In FIG. 3A, diagram 300A of a Tetrahedron beam CT (TBCT) is shown. The example TBCT may be a volumetric CT based on a linear array x-ray source including an MPTEX tube 304. In some embodiments, linear x-ray source array and detector array may be mounted on a rotating gantry orthogonally, for example. Each beam may be collimated by a multi-slot collimator 302 to a narrow fan beam and received by the detector after passing through the patient at PCD 310. Due to engineering difficulty, the linear array x-ray sources may use a fixed anode. Despite sequential scanning of the sources, the linear array x-ray source still cannot operate at high power due to the use of a fixed anode. Therefore, current TBCT is limited to the scanning of small objects, such as head phantom 306, rotating slowly on rotation stage 308.

Figure 3B:
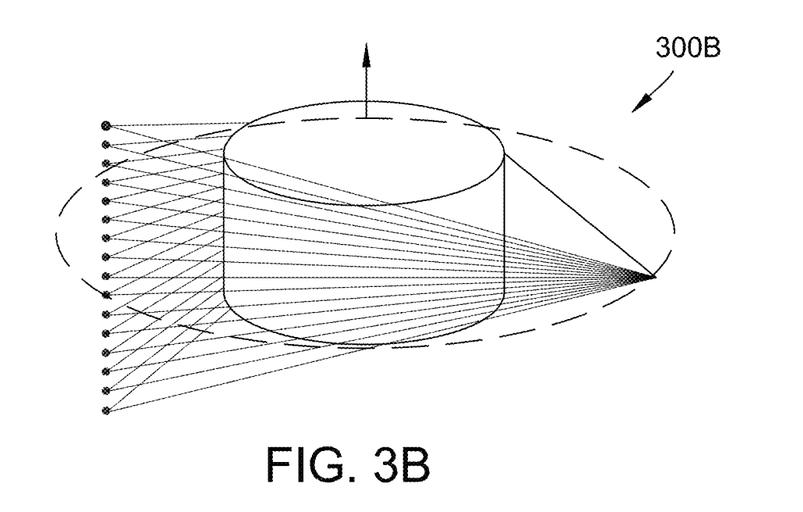
Figure 3C:
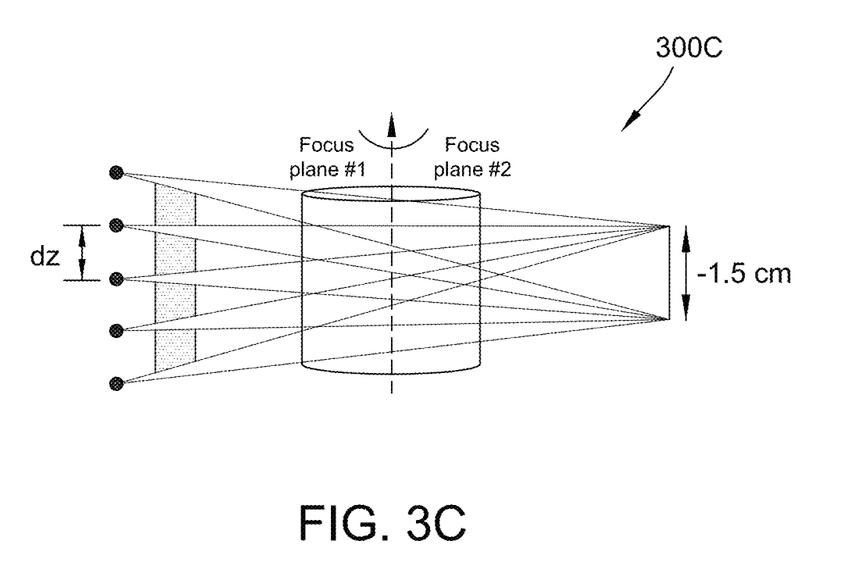

In some embodiments, and in reference to diagrams 300B and 300C in FIGS. 3B and 3C, respectively, the TBCT may employ a linear x-ray source array that generates a stack of fan beam x-ray received by a linear array detector. Compared with cone beam CT, TBCT is immune to the x-ray scattering problems and can use the same high quality CT detector as helical CT. However, it is challenging to develop linear array x-ray source with a rotating anode. Current linear array x-ray sources employ an elongated fixed anode. Thereby its power is limited and the TBCT can only scan small object with a low speed.

Figure 4:
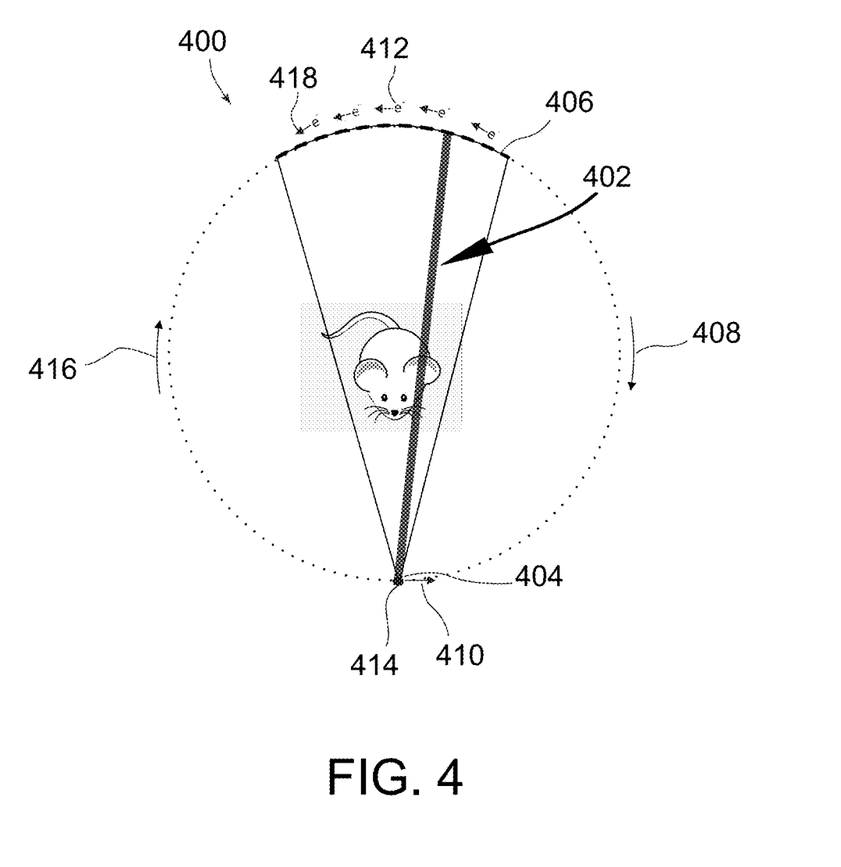
FIG. 4 illustrates exemplary synchronized focal spot and detector signal movement with gantry rotation.

FIG. 4 illustrates a diagram 400 of an exemplary synchronized focal spot 414 and detector signal movement with gantry rotation 416. For example, a source 404 and detector 406 rotates together around the imaging subject clockwise 408. Each source and detector pair may sample the tissue along a line 402. In a traditional CT system, the line 402 may move slightly during a projection measurement due to the system rotation 408. In this example, the source 404 may move in the opposite direction of the gantry rotation 416. The signal or charge 412 in the detector may also shift in the opposite direction of the gantry rotation 416. When the focal spot translation 410 and detector signal shift 418 have the same speed as gantry rotation 408, the sampling line 402 will remain static during a projection measurement and avoid motion blurring during projection measurement.

In some embodiments, due to the static sampling, the detector does not need to sample at very high speed. Thereby, less number of projection measurement may be acquired. Less projection measurement may allow fast image reconstruction and reduce the computational cost. Or it may allow more complicated iterative reconstruction such as optics-model based reconstruction.

In some embodiments, aside from reducing motion blurring, the systems and methods provided may allow for higher tube power because the focal spot may move on the target instead of staying in the same spot. For example, for a fixed anode source, the dwell duration may be equal to the focal spot width divided by the gantry speed. The faster the gantry speed and the smaller the focal spot, the shorter the dwell duration and the higher tube power will be. For example, for a CT with 3 rev/s gantry rotation speed and the source is mounted at 65 cm to the rotation axis, the linear speed of the source will be 12 m/s. The dwell duration will be less than 0.1 ms with 1 mm focal spot size. Despite shorter dwell duration, this synchronized focal spot and gantry rotation technique should be used on either rotating anode tube or the linear array x-ray tube. As shown in plot 100B of FIG. 1B, for example, the focal spot needs certain time to cool down after a temperature spike. With only one focal spot, there may be not enough time to allow focal spot temperature returning to its base temperature.

In some embodiments, with respect to diagram 300B of FIG. 3B, in TBCT, besides sequential scanning, each x-ray focal spot may move laterally via focal spot translation 410 as shown in FIG. 4. TBCT with focal spots movement synchronized gantry rotation may achieve much higher power. This may require gantry to rotate at a high speed. TBCT may also use the same gantry as helical CT (see FIG. 2A). Without rotating anode, the linear array x-ray source with moving focal spot may have a lower cost and longer lifetime due to its simple structure design. Also, without bearing, the fixed anode may have direct contact with the tube housing and the heat can be conducted out rapidly.

As shown in FIG. 4, in helical CT, the focal spot may move in the opposite direction of the anode rotating. The focal spot speed, which equals to gantry rotation speed, may be superimposed on the anode rotation speed. This may further reduce the dwell duration and increase tube power.

Figure 5:
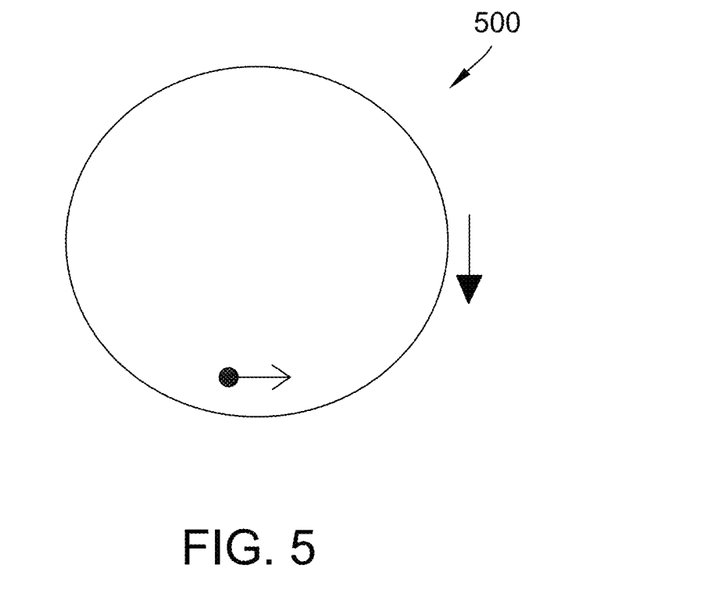
FIG. 5 is an exemplary diagram of a moving focal spot on a rotating anode.

FIG. 5 illustrates an exemplary diagram 500 of a moving focal spot on a rotating anode. The focal spot scanning may be achieved by deflecting the electron beam by electric or magnetic field. FIG. 5 shows the diagram 500 of moving focal spot on a rotating anode. The focal spot moves in one direction against the anode rotation direction.

The shift of detector signal may be achieved by a time-delay-integration (TDI) method. The data of each detector row or column may be shifted and added by row-by-row or column-by-column before reading out in frame mode.

Figure 6:
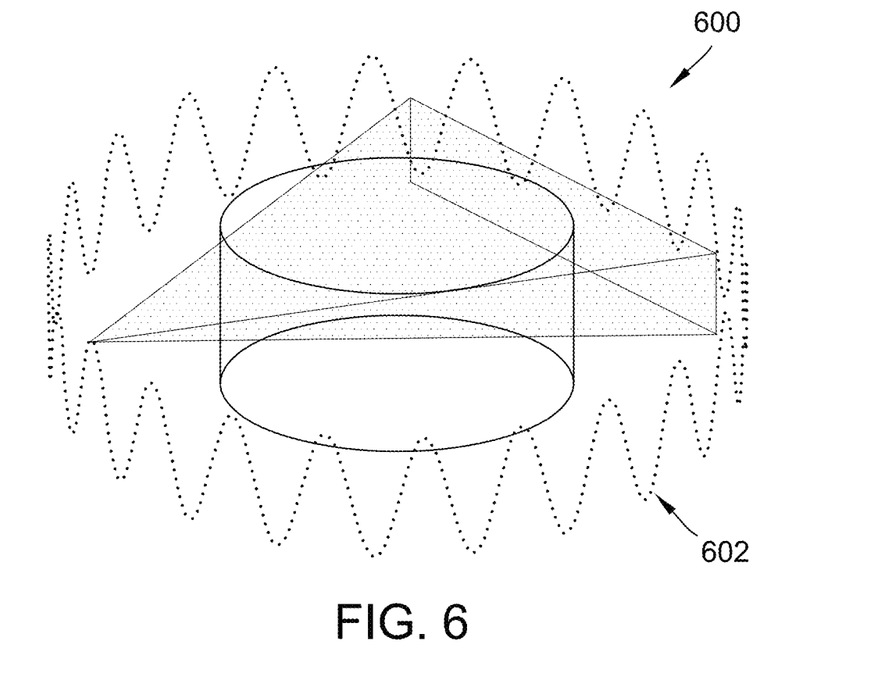
FIG. 6 is an exemplary cone-beam system having a linear array x-ray source.

FIG. 6 illustrates an exemplary cone-beam CT system 600 having a linear array x-ray source. Besides helical CT and TBCT, CBCT may also be used. FIG. 6 shows a cone-beam CT system with a linear array x-ray source. The system is similar to TBCT except the detector is wider and the x-ray beam has a cone-shape. The source scans sequentially while rotating slowly about the subject. The source trajectory has a saddle trajectory 602. The design may satisfy data sufficient condition and may perform exact image reconstruction, unlike traditional CBCT and TBCT that can only reconstruct approximately. The focal spot scanning technique can solve the power limitation of the linear array x-ray source with a fixed gantry.

Figure 7:
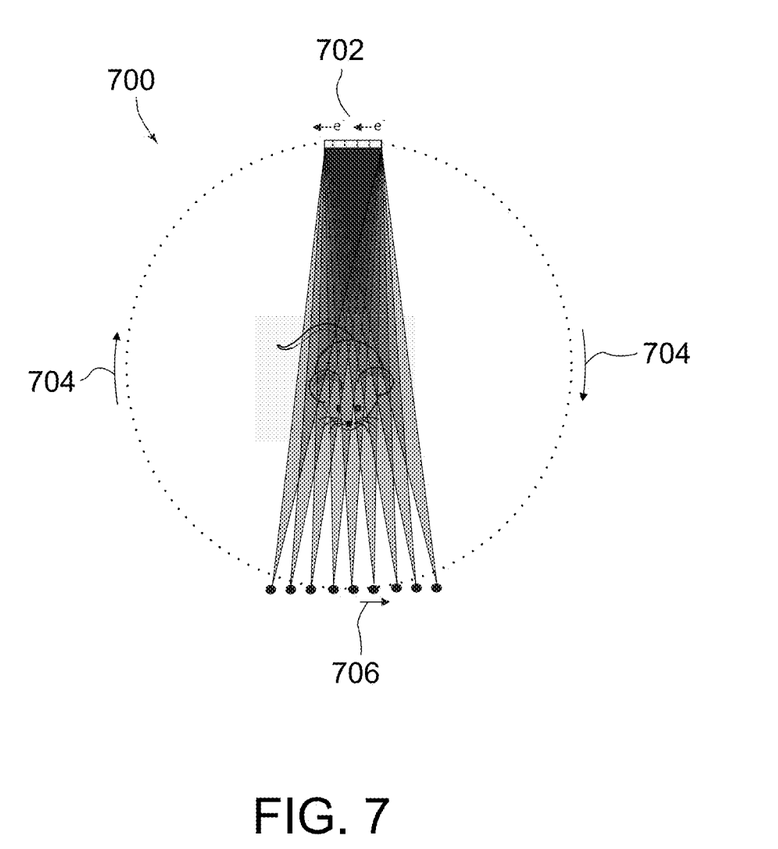
FIG. 7 is an exemplary configuration in which a source array is positioned in a rotation plane and a detector array is positioned orthogonal to the rotation plane.

FIG. 7 illustrates an exemplary configuration 700 in which a source array is positioned in a rotation plane 704 and a detector array is positioned orthogonal to the rotation plane. In some linear array source designs, it is easier to move focal spot in the array direction. FIG. 7 shows another exemplary configuration in which the source array may be positioned in the rotation plane and the detector array may be orthogonal to the rotation plane. The detector signal may shift 702 in row direction and the focal spots may move in its length direction 706.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, the terms "a" and "an" and "the" and similar references used in the context of describing a particular embodiment (especially in the context of certain of the following claims) are construed to cover both the singular and the plural, unless specifically noted otherwise. In some embodiments, the term "or" as used herein, including the claims, is used to mean "and/or" unless explicitly indicated to refer to alternatives only or to refer to the alternatives that are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and may also cover other unlisted steps. Similarly, any composition or device that "comprises," "has" or "includes" one or more features is not limited to possessing only those one or more features and may cover other unlisted features.

All methods described herein are performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member is referred to and claimed individually or in any combination with other members of the group or other elements found herein. One or more members of a group are included in, or deleted from, a group for reasons of convenience or patentability. When any such inclusion or deletion occurs, the specification is herein deemed to contain the group as modified thus fulfilling the written description of all Markush groups used in the appended claims.

To facilitate the understanding of the embodiments described herein, a number of terms are defined below. The terms defined herein have meanings as commonly understood by a person of ordinary skill in the areas relevant to the present disclosure. Terms such as "a," "an," and "the" are not intended to refer to only a singular entity, but rather include the general class of which a specific example may be used for illustration. The terminology herein is used to describe specific embodiments of the disclosure, but their usage does not delimit the disclosure, except as outlined in the claims.

All of the compositions and/or methods disclosed and claimed herein may be made and/or executed without undue experimentation in light of the present disclosure. While the compositions and methods of this disclosure have been described in terms of the embodiments included herein, it will be apparent to those of ordinary skill in the art that variations may be applied to the compositions and/or methods and in the steps or in the sequence of steps of the method described herein without departing from the concept, spirit, and scope of the disclosure. All such similar substitutes and modifications apparent to those skilled in the art are deemed to be within the spirit, scope, and concept of the disclosure as defined by the appended claims.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for performing computed tomography (CT) producing x-ray photons with an x-ray source;
   moving focal spots in a same speed and an opposite direction of a gantry rotation;
   performing projection measurement with a 2D detector while the focal spots move in a same speed and an opposite direction of the gantry rotation; and
   shifting data in the same speed and the opposite direction of the gantry rotation using a time-delay-integration detector,
   wherein the x-ray source and the 2D detector are mounted on the gantry, and moving the focal spots comprises moving a focal spot of the focal spots in a saddle trajectory and moving the focal spot in the same speed and opposite direction of the gantry rotation during each sampling or projection measurement.

2. The method of claim 1, further comprising rotating a gantry in a gantry rotation direction.

3. The method of claim 1, wherein the x-ray source comprises a rotating anode and a focal spot of the focal spots, and moving the focal spots comprises repeatedly moving the focal spot in an opposite direction of the rotating anode about the center of the focal spot.

4. The method of claim 1, wherein the x-ray source comprises a linear array x-ray source including a fixed anode, and moving the focal spots comprises repeatedly moving the focal spots orthogonal to an array direction about the respective centers of the focal spots.

5. The method of claim 1, wherein the x-ray source comprises a linear array x-ray source including a fixed anode, and moving the focal spots comprises repeatedly moving the focal spots in an array direction about the respective centers of the focal spots.

* * * * *